*(12)* United States Patent
Gatti-Lafranconi et al.

(10) Patent No.: US 11,584,962 B2
(45) Date of Patent: Feb. 21, 2023

(54) COMPOSITIONS FOR USE IN POLYNUCLEOTIDE SEQUENCING

(71) Applicant: Illumina Cambridge Limited, Cambridge (GB)

(72) Inventors: Pietro Gatti-Lafranconi, Cambridge (GB); Helen Sansom, Cambridge (GB); Matthew Hancock, Cambridge (GB)

(73) Assignee: ILLUMINA CAMBRIDGE LIMITED, Cambridge (GB)

( * ) Notice: Subject to any disclaimer, the term of this patent is extended or adjusted under 35 U.S.C. 154(b) by 310 days.

(21) Appl. No.: 16/710,634

(22) Filed: Dec. 11, 2019

(65) Prior Publication Data

US 2020/0190569 A1     Jun. 18, 2020

Related U.S. Application Data

(60) Provisional application No. 62/780,746, filed on Dec. 17, 2018.

(51) Int. Cl.
*C12Q 1/6869* (2018.01)
*B01L 3/00* (2006.01)

(52) U.S. Cl.
CPC ............ *C12Q 1/6869* (2013.01); *B01L 3/508* (2013.01); *B01L 2200/16* (2013.01)

(58) Field of Classification Search
CPC .............................. C12Q 1/6869; B01L 3/508
See application file for complete search history.

(56) References Cited

U.S. PATENT DOCUMENTS

| | | | |
|---|---|---|---|
| 9,115,353 B2 | 8/2015 | Klausing et al. | |
| 9,217,178 B2 | 12/2015 | Fedurco et al. | |
| 9,765,384 B2 | 9/2017 | Olejnik et al. | |
| 10,036,011 B2 | 7/2018 | Andruzzi et al. | |
| 11,293,061 B2 * | 4/2022 | Francais | ................. C07H 19/20 |
| 2003/0215862 A1 * | 11/2003 | Parce | ................... C12Q 1/6869 435/91.2 |
| 2018/0127809 A1 | 5/2018 | Andruzzi et al. | |
| 2018/0148781 A1 | 5/2018 | Andruzzi et al. | |

FOREIGN PATENT DOCUMENTS

WO     WO-2014139596 A1 *    9/2014    ........... C07H 19/073

OTHER PUBLICATIONS

Bansal et al, Bioreducible polyethylenimine nanoparticles for the efficientdelivery of nucleic acids, 2015, Org. Biomol. Chem., 13, 3128-3135 (Year: 2015).*
Costello et al, Discovery and characterization of artifactual mutations in deep coverage targeted capture sequencing data due to oxidative DNA damage during sample preparation, 2013, Nucleic Acids Research, 41, No. 6 e67, pp. 1-12 (Year: 2013).*
Biewenga, et al., "The Pharmacology of the Antioxidant Lipoic Acid", Gen. Pharmac., vol. 29, No. 3, 1997, 315-331.

* cited by examiner

*Primary Examiner* — Narayan K Bhat
(74) *Attorney, Agent, or Firm* — Mueting Raasch Group

(57) ABSTRACT

A polynucleotide sequencing method comprises (i) removing a label and a blocking moiety from a blocked, labeled nucleotide incorporated into a copy polynucleotide strand that is complementary to at least a portion of a template polynucleotide strand; and (ii) washing the removed label and blocking moiety away from the copy strand with a wash solution comprising a first buffer comprising a scavenger compound. Removing the label and blocking moieties may comprise chemically removing the moieties. The first buffer may also comprise an antioxidant and may be used in a scanning buffer used during a nucleotide detection step.

11 Claims, 7 Drawing Sheets

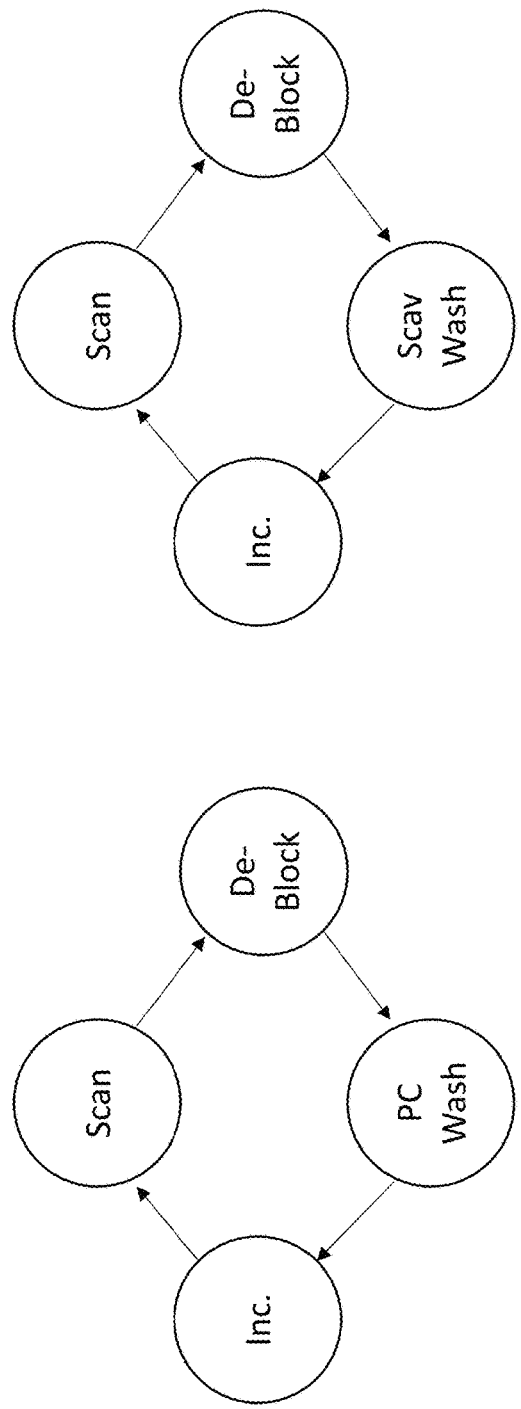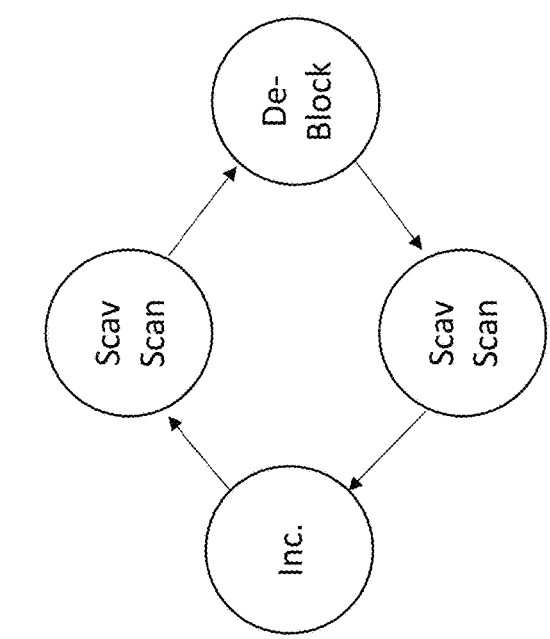

COMPOSITIONS FOR USE IN POLYNUCLEOTIDE SEQUENCING

PRIORITY

This application claims the benefit of U.S. Provisional Application No. 62/780,746, filed Dec. 17, 2018, the disclosure of which is incorporated by reference herein in its entirety.

FIELD

The present disclosure relates to, among other things, sequencing of polynucleotides.

INTRODUCTION

Sequencing of a template polynucleotide strand may occur through multiple cycles of steps by which one detectable nucleotide per cycle is incorporated into a copy strand complementary to the template strand. The detectable nucleotides are typically blocked to prevent incorporation of more than one detectable nucleotide per cycle. After an incubation time, a wash step is typically performed to remove any unincorporated detectable nucleotide. A detection step, in which the identity of the detectable nucleotide incorporated into the copy strand is determined, may then performed. Next, an unblocking step and cleavage or masking step is performed in which the blocking agent is removed from the last incorporated nucleotide in the copy strand, and the detectable moiety is cleaved from or masked on the last nucleotide incorporated into the copy strand. In some instances, the step of removing the blocking moiety also removes the detectable moiety. The cycle is then repeated by introducing blocked, detectable nucleotides in an incorporation step.

Various compositions are employed at each step of a cycle of sequencing. For example, an incorporation composition comprising a polymerase and nucleotides are employed during the incorporation step. A scan composition that may include, among other things, an antioxidant to protect the polynucleotides from photo-induced damage during the detection step when, for example, the nucleotides include fluorophore labels for detection. A de-blocking composition that includes reagents for cleaving the blocking moiety from the nucleotide incorporated is employed during the de-blocking step. A post-cleave wash composition that may include a scavenger compound to protect the polynucleotides, enzymes or other sequencing reagents from reactive compounds used in, or resulting from, the de-blocking step may be used following the de-blocking step.

A great deal of trial and error and consideration is typically employed to develop the compositions used at each step of sequencing to optimize performance.

SUMMARY

The present disclosure describes, among other things, polynucleotide sequencing methods that employ a single composition for both the detection step and the post-cleave wash step. When the same composition is used for the detection step and the post-cleave wash step, the number of compositions used in the sequencing process may be reduced, which may provide one or more advantage. For example, reducing the number of reagents or compositions may reduce the burden of ensuring good manufacturing practices and composition or reagent stability for multiple compositions. Furthermore, the use of fewer compositions during sequencing may reduce the complexity of the sequencing instruments and components used with the sequencing instruments, which may improve the reliability of the instruments and components.

In some embodiments described herein, a polynucleotide sequencing method comprises (a) incorporating a blocked, labeled nucleotide into a copy polynucleotide strand complementary to at least a portion of a template polynucleotide strand; (b) detecting the identity of the blocked, labeled nucleotide in the presence of a first buffer composition; (c) removing a label and blocking moiety from the blocked, labeled nucleotide incorporated into the copy strand; and (d) washing the removed label and blocking moiety away from the copy strand with a wash solution comprising the first buffer composition. The first buffer composition comprises an antioxidant and a scavenger compound. Steps (a) to (d) may be repeated until a sequence of the portion of the template polynucleotide strand is determined.

In some embodiments described herein, a cartridge for use with a sequencing apparatus comprises a plurality of plurality of chambers containing a plurality of compositions. Each chamber contains a single composition, wherein the compositions consist of: (a) reagents for incorporating a blocked, labeled nucleotide into a copy polynucleotide strand complementary to at least a portion of a template polynucleotide strand; (b) a buffer composition comprising an antioxidant and a scavenger; (c) reagents for chemically removing a label and blocking moiety from the blocked, labeled nucleotide incorporated into the copy strand; and (d) a wash buffer.

In some embodiments described herein, a kit for use with a sequencing apparatus, comprises a plurality of chambers containing a plurality of compositions. Each chamber contains a single composition, wherein the compositions consist of: (a) reagents for incorporating a blocked, labeled nucleotide into a copy polynucleotide strand complementary to at least a portion of a template polynucleotide strand; (b) a buffer composition comprising an antioxidant and a scavenger; (c) reagents for chemically removing a label and blocking moiety from the blocked, labeled nucleotide incorporated into the copy strand; and (d) a wash buffer.

The present disclosure also describes a post cleave wash composition that includes 3,3'-dithiodipropionic acid (DPPA) as a scavenger. As illustrated herein, DPPA may provide improved performance relative to currently employed scavengers, such as lipoic acid. The improvements may be particularly effective when performing a sequencing method that employs a single composition for the scanning step and the post-cleave wash step. The use of effective scavengers may protect polynucleotides, enzymes, or other sequencing compounds from damage due to reagents or reaction products associated with the de-blocking step. By preventing damage to polynucleotides, enzymes, or other sequencing components during sequencing, longer runs (more cycles) of sequence may be completed before the signal degrades.

In some embodiments described herein, a polynucleotide sequencing method comprises (i) removing a label and a blocking moiety from a blocked, labeled nucleotide incorporated into a copy polynucleotide strand that is complementary to at least a portion of a template polynucleotide strand; and (ii) washing the removed label and blocking moiety away from the copy strand with a wash solution comprising a scavenger compound. The scavenger compound comprises DPPA. Removing the label and blocking moieties may comprise chemically removing the moieties.

The details of one or more embodiments are set forth in the accompanying drawings and the description below. Other features, objects, and advantages will be apparent from the description and drawings, and from the claims.

It is to be understood that both the foregoing general description and the following detailed description present embodiments of the subject matter of the present disclosure and are intended to provide an overview or framework for understanding the nature and character of the subject matter of the present disclosure as it is claimed. The accompanying drawings are included to provide a further understanding of the subject matter of the present disclosure and are incorporated into and constitute a part of this specification. The drawings illustrate various embodiments of the subject matter of the present disclosure and together with the description serve to explain the principles and operations of the subject matter of the present disclosure. Additionally, the drawings and descriptions are meant to be merely illustrative and are not intended to limit the scope of the claims in any manner.

DESCRIPTION OF DRAWINGS

The following detailed description of specific embodiments of the present disclosure may be best understood when read in conjunction with the following drawings.

FIGS. 1-3 are schematic diagrams of some steps of sequencing processes illustrating some compositions employed at the various steps.

Figure 5:
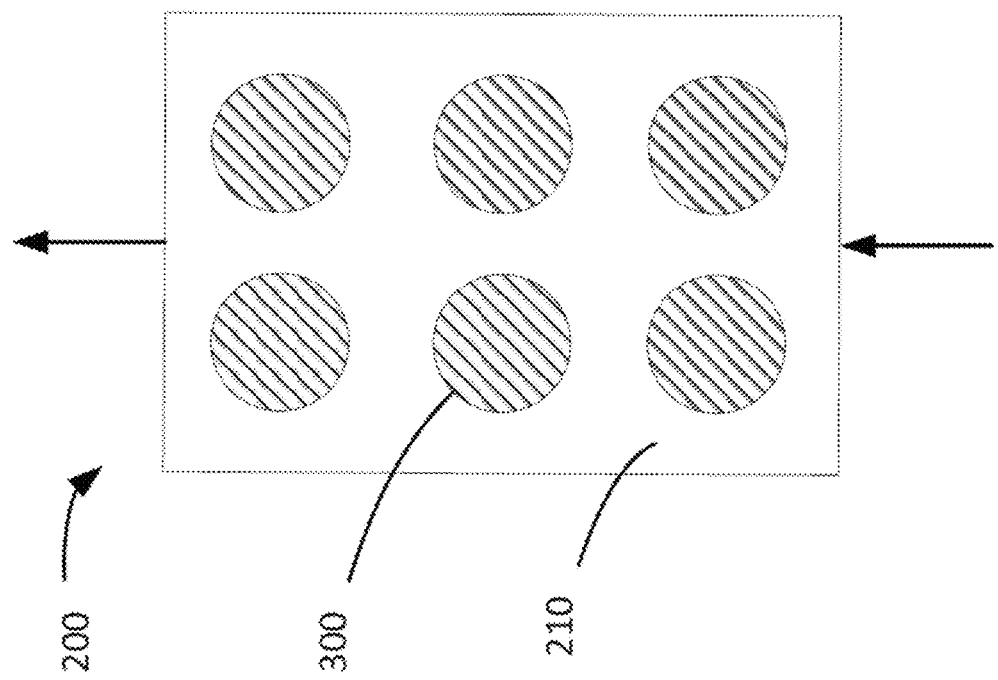
FIG. 5 is a schematic plan view of an embodiment of a flow cell that may be employed in accordance with the teachings presented herein.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar to other numbered components.

DETAILED DESCRIPTION

Reference will now be made in greater detail to various embodiments of the subject matter of the present disclosure, some embodiments of which are illustrated in the accompanying drawings.

All scientific and technical terms used herein have meanings commonly used in the art unless otherwise specified. The definitions provided herein are to facilitate understanding of certain terms used frequently herein and are not meant to limit the scope of the present disclosure.

As used herein, singular forms "a," "an" and "the" include plural referents unless the context clearly dictates otherwise. Thus, for example, reference to a "template polynucleotide sequence" includes examples having two or more such "template polynucleotide sequences" unless the context clearly indicates otherwise.

As used in this specification and the appended claims, the term "or" is generally employed in its sense including "and/or" unless the content clearly dictates otherwise. The term "and/or" means one or all of the listed elements or a combination of any two or more of the listed elements. The use of "and/or" in some instances does not imply that the use of "or" in other instances may not mean "and/or."

As used herein, "have", "has", "having", "include", "includes", "including", "comprise", "comprises", "comprising" or the like are used in their open-ended inclusive sense, and generally mean "include, but not limited to", "includes, but not limited to", or "including, but not limited to".

"Optional" or "optionally" means that the subsequently described event, circumstance, or component, can or cannot occur, and that the description includes instances where the event, circumstance, or component, occurs and instances where it does not.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the inventive technology.

In addition, the recitations herein of numerical ranges by endpoints include all numbers subsumed within that range (e.g., 1 to 5 includes 1, 1.5, 2, 2.75, 3, 3.80, 4, 5, etc.). Where a range of values is "greater than", "less than", etc. a particular value, that value is included within the range.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that any particular order be inferred. However, it will be understood that a presented order is one embodiment of an order by which the method may carried out. Any recited single or multiple feature or aspect in any one claim may be combined or permuted with any other recited feature or aspect in any other claim or claims.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method comprising an incorporation step, a detection step, a deprotection step, and one or more wash steps includes embodiments where the method consists of enumerated steps and embodiments where the method consists essentially of the enumerated.

As used herein, "providing" in the context of a compound, composition, or article means making the compound, composition, or article, purchasing the compound, composition or article, or otherwise obtaining the compound, composition or article.

As used herein, the term "chain extending enzyme" is an enzyme that produces a copy replicate of a polynucleotide using the polynucleotide as a template strand. For example, the chain extending enzyme may be an enzyme having polymerase activity. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases may use a short RNA or DNA strand, called a primer, to begin strand growth. Some polymerases may displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "primer" and its derivatives refer generally to any polynucleotide that may hybridize to a target sequence of interest. Typically, the primer functions as a substrate onto which nucleotides may be polymerized by a polymerase; in some embodiments, however, the primer may become incorporated into the synthesized polynucleotide strand and provide a site to which another primer may hybridize to prime synthesis of a new strand that is complementary to the synthesized nucleic acid molecule. The primer may be comprised of any combination of nucleotides or analogs thereof. In some embodiments, the primer is a single-stranded oligonucleotide or polynucleotide.

The terms "polynucleotide" and "oligonucleotide" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). As used herein, "amplified target sequences" and its derivatives, refers generally to a polynucleotide sequence produced by the amplifying the target sequences using target-specific primers and the methods provided herein. The amplified target sequences may be either of the same sense (i.e the positive strand) or antisense (i.e., the negative strand) with respect to the target sequences.

Suitable nucleotides for use in the provided methods include, but are not limited to, deoxynucleotide triphosphates, deoxyadenosine triphosphate (dATP), deoxythymidine triphosphate (dTTP), deoxycytidine triphosphate (dCTP), and deoxyguanosine triphosphate (dGTP). Optionally, the nucleotides used in the provided methods, whether labeled or unlabeled, can include a blocking moiety such as a reversible terminator moiety that inhibits chain extension. Suitable labels for use on the labeled nucleotides include, but are not limited to, haptens, radionucleotides, enzymes, fluorescent labels, chemiluminescent labels, and chromogenic agents.

A polynucleotide will generally contain phosphodiester bonds, although in some cases nucleic acid analogs can have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Polynucleotides containing one or more carbocyclic sugars are also included within the definition of polynucleotides (see Jenkins et al., Chem. Soc. Rev. (1995) pp169-176). Several polynucleotide analogs are described in Rawls, C & E News Jun. 2, 1997 page 35. All these references are hereby expressly incorporated by reference. These modifications of the ribose-phosphate backbone may be done to facilitate the addition of labels, or to increase the stability and half-life of such molecules in physiological environments.

A polynucleotide will generally contain a specific sequence of four nucleotide bases:

adenine (A); cytosine (C); guanine (G); and thymine (T). Uracil (U) can also be present, for example, as a natural replacement for thymine when the nucleic acid is RNA. Uracil can also be used in DNA. A polynucleotide may also include native or non-native bases. In this regard, a native deoxyribonucleic acid polynucleotide may have one or more bases selected from the group consisting of adenine, thymine, cytosine or guanine and a ribonucleic acid may have one or more bases selected from the group consisting of uracil, adenine, cytosine or guanine. It will be understood that a deoxyribonucleic acid polynucleotide used in the methods or compositions set forth herein may include, for example, uracil bases and a ribonucleic acid can include, for example, a thymine base. Exemplary non-native bases that may be included in a nucleic acid, whether having a native backbone or analog structure, include, without limitation, inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. Optionally, isocytosine and isoguanine may be included in a nucleic acid in order to reduce non-specific hybridization, as generally described in U.S. Pat. No. 5,681,702, which is incorporated by reference herein in its entirety.

A non-native base used in a polynucleotide may have universal base pairing activity such that it is capable of base pairing with any other naturally occurring base. Exemplary bases having universal base pairing activity include 3-nitropyrrole and 5-nitroindole. Other bases that can be used include those that have base pairing activity with a subset of the naturally occurring bases such as inosine, which basepairs with cytosine, adenine or uracil.

Incorporation of a nucleotide into a polynucleotide strand refers to joining of the nucleotide to a free 3 ' hydroxyl group of the polynucleotide strand via formation of a phosphodiester linkage with the 5' phosphate group of the nucleotide. The polynucleotide template to be sequenced can be DNA or RNA, or even a hybrid molecule that includes both deoxynucleotides and ribonucleotides. The polynucleotide can include naturally occurring and/or non-naturally occurring nucleotides and natural or non-natural backbone linkages.

The present disclosure describes, among other things, polynucleotide sequencing methods and compositions for use in the sequencing methods. The methods and compositions may allow for longer sequencing runs, shorter cycle times, or longer sequencing runs and shorter cycle times.

The present disclosure also describes, polynucleotide sequencing methods, compositions, kits, and cartridges that employ fewer compositions than current sequencing methods. Employing fewer compositions may provide a number of advantages including potential decreased overall cost of goods and improved reliability of the sequencing methods and instrumentation. In particular, the present disclosure describes a composition that may be used during a detection step and during a post-cleave wash step. The composition includes an antioxidant to protect oligonucleotides and polynucleotides from photo-induced damage during a scanning step to detect nucleotide identity. The composition also includes a scavenger to protect the oligonucleotide, polynucleotides, enzymes, and other reagents from reactive compounds that may be used in, or result from, the deblocking step.

Among other things, the present disclosure describes a post-cleave wash composition that includes 3,3'-dithiodipropionic acid (DPPA) as a scavenger. DPPA may provide improved performance relative to currently employed scavengers, such as lipoic acid. DPPA may be present in a composition that also includes an antioxidant so that the composition may be used in both the scanning step and the post-cleave wash step.

Removing the blocking moiety during a de-blocking step preferably also results in removal of a labeled moiety. In some embodiments, the blocking moiety comprises the labeled moiety. In some embodiments, the blocking moiety is chemically removed. For purposes of the present disclosure, "chemical" removal of a blocking moiety involves a chemical reaction between a cleavage agent and the blocked nucleotide to cause the blocking moiety to be removed from the nucleotide. For purposes of this disclosure, chemical removal of the blocking moiety does not include removal of the blocking moiety in a process that involves only heat, only light, or only heat and light. Chemical removal of the blocking moiety also does not include enzymatic removal for purposes of the present disclosure.

Preferably the blocking moiety and the labeled moiety are both cleaved by the same process when blocking moiety and the labeled moiety are separate moieties. For example, the blocking moiety and the labeled moiety may be bound to the nucleotide by the same or similar linking groups, which may be cleaved or removed by the same reagents or conditions. This will make the deblocking and de-labeling process more efficient, as only a single treatment will be required to remove both the label and the block. The blocking moiety and the labeled moiety may, of course, be cleaved under entirely different chemical conditions.

The wash composition comprises a scavenger compound that inhibits interaction of reactive compounds used in or resulting from the deblocking step with polynucleotides, enzymes, or other compounds used in or generated from the sequencing process. Accordingly, the presence of the scavenger compounds may reduce damage to the polynucleotides, enzymes, or other compounds, which may allow for additional cycles of sequencing to be performed relative to sequencing processes that do not include the scavenger compound in the wash composition.

The scavenger compound used in the wash composition may depend on the reagents employed in the deblocking step, the reaction products produced from the deblocking step, or the reagents employed in the deblocking step and the reaction products produced from the deblocking step, which may depend on the linker used to attach the blocking moiety, the labeled moiety, or the blocker moiety and the linker moiety to the nucleotide.

The blocking moiety, the labeled moiety, or the blocking moiety and the labeled moiety molecule may be linked to the nucleotide by any suitable linker. The linker may comprise one or more cleavable groups including, but not limited to, disulfide, diol, diazo, ester, sulfone azide, alyl and silyl ether, azide and alkoxy groups. In preferred embodiments, the linker comprises one or more of an azide, an alkoxy, and a disulfide group as a linker. Incorporation of a disulfide bond into a linker may be accomplished in a number of ways, for example as described in U.S. Pat. No. 7,771,973 or as described in Hermanson, Bioconjugate Techniques, Second Edition, Academic Press (incorporated herein by reference in their entireties).

More generally, suitable linkers include, but are not limited to, disulfide linkers, acid labile linkers (including dialkoxybenzyl linkers, Sieber linkers, indole linkers, and t-butyl Sieber linkers), electrophilically cleavable linkers, nucleophilically cleavable linkers, photocleavable linkers, cleavage under reductive conditions, oxidative conditions, cleavage via use of safety-catch linkers, and cleavage by elimination mechanisms.

Any suitable electrophilically cleavable linkers may be employed. Electrophilically cleavable linkers are typically cleaved by protons and include cleavages sensitive to acids. Suitable electrophilically cleavable linkers include the modified benzylic systems such as trityl, p-alkoxybenzyl esters and p-alkoxybenzyl amides. Other suitable electrophilically cleavable linkers include tert-butyloxycarbonyl (Boc) groups and the acetal system.

The use of thiophilic metals, such as nickel, silver or mercury, in the cleavage of thioacetal or other sulfur-containing protecting groups can also be considered for the preparation of suitable electrophilically cleavable linkers molecules.

Any suitable nucleophilic cleavage linker may be employed. Nucleophilic cleavage is a well-recognized method in the preparation of linker molecules. Groups such as esters that are labile in water (i.e., can be cleaved simply at basic pH) and groups that are labile to non-aqueous nucleophiles, may be used. Fluoride ions may be used to cleave silicon-oxygen bonds in groups such as triisopropyl silane (TIPS) or t-butyldimethyl silane (TBDMS).

Any suitable photocleavable linker may be used. Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenzyl compounds and nitroveratryl compounds. Linkers based on benzoin chemistry may also be used (Lee et al., J. Org. Chem. 64:3454-3460, 1999).

Any suitable linker that cleaves under reductive conditions may be used. There are known many linkers that are susceptible to reductive cleavage. For example, catalytic hydrogenation using palladium-based catalysts has been used to cleave benzyl and benzyloxycarbonyl groups. By way of further example, disulfide bond reduction is also known in the art.

Any suitable linker that cleaves under oxidative conditions may be used. Oxidation-based approaches are well known in the art. These include oxidation of p-alkoxybenzyl groups and the oxidation of sulfur and selenium linkers. The use of aqueous iodine to cleave disulfides and other sulfur or selenium-based linkers is also within the scope of the invention.

Any suitable safety-catch linker may be used. Safety-catch linkers are those that cleave in two steps. In a preferred system, the first step is the generation of a reactive nucleophilic center followed by a second step involving an intramolecular cyclization that results in cleavage. For example, levulinic ester linkages may be treated with hydrazine or photochemistry to release an active amine, which may then be cyclized to cleave an ester elsewhere in the molecule (Burgess et al., J. Org. Chem. 62:5165-5168, 1997).

Any suitable linker that may be cleaved by elimination mechanisms may be used. For example, the base-catalyzed elimination of groups such as Fmoc and cyanoethyl, and palladium-catalyzed reductive elimination of allylic systems, may be used.

The linkers may include one or more spacer in addition to the cleavage site. The spacer distances e.g., the nucleotide base from the cleavage site or label or blocking moiety. The length of the linker is generally not important provided that the nucleotide may be incorporated into the copy strand after by a chain extending enzyme after the blocking moiety is cleaved.

Examples of suitable linkers, nucleotides, blocking moieties that may be employed are described in U.S. Pat. No. 7,541,444; WO 03/048387; US 2013/0079232A1; and U.S. Pat. No. 7,414,116, each of which is hereby incorporated herein in their respective entireties to the extent that they do not conflict with the present disclosure. Particularly preferred linkers are phosphine-cleavable azide containing linkers. The labeled moiety may comprise a fluorophore.

A cleavage agent may be added at an appropriate time to the sequencing procedure to cleave a cleavage group in a linker to remove the blocking moiety, the labeled moiety, or the blocking moiety and the labeled moiety from the nucleotide incorporated into the copy strand. For example, the cleavage agent may be added after detection of the identity of the nucleotide incorporated into the copy strand in the current cycle of sequencing. The cleavage agent added is dependent on the cleavage group present. For example, cleavage of disulfide bonds or other reductive cleavage groups may be accomplished by a reducing agent. Reduction of a disulfide bond results in the release of the linked molecule from the nucleotide. Reducing agents useful in practicing embodiments as described herein include, but are not limited to, phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol and tris(2-carboxyethyl)phosphine (TCEP), tris(hydroxymethyl)phosphine (THP) and β-[tris(hydroxymethyl)phosphine]propionic acid (THPP). In some embodiments, a reducing agent used for cleaving a disulphide bond in a linker as described herein is DTT. In some embodiments, the concentration of a reducing reagent, for example DTT, utilized for cleaving a disulfide bond is at least 1 to 1000 mM, at least 20 to 800 mM, at least 40 to 500 mM, and preferably at least 50 to 200 mM.

In some embodiments, a reducing agent used for cleaving a disulphide bond in a linker or a cleavable linker comprising an allyl or azido group is a phosphine reagent, a water-soluble phosphine reagent, a nitrogen containing phosphine reagent and salts and derivatives thereof. Exemplary phosphine reagents include, but are not limited to, tris(2-carboxyethyl)phosphine (TCEP), tris(hydroxypropyl)phosphine (THP), tris(hydroxymethyl)phosphine (TMP) and those disclosed in US patent publication 2009/0325172 (incorporated herein by reference in its entirety) such as triaryl phosphines, trialkyl phosphines, sulfonate containing and carboxylate containing phosphines and derivatized water soluble phosphines. Other phosphines that may be used as cleavage agents include those described in U.S. Pat. No. 7,414,116, which is hereby incorporated herein by reference in its entirety to the extent that it does not conflict with the present disclosure. In some embodiments, the concentration of a phosphine utilized is from about 0.5 mM to about 500 mM, such as from about 5 mM to about 50 mM, and preferably from about 10 mM to about 40 mM. Methods and compositions as described herein are not limited by any particular cleavage group and alternatives will be readily apparent to a skilled artisan and are considered within the scope of the present disclosure.

The skilled person will appreciate how to attach a suitable blocking group to a ribose ring of a nucleotide to block interactions with the 3'-OH. The blocking group may be attached directly at the 3' position or may be attached at the 2' position (the blocking group being of sufficient size or charge to block interactions at the 3' position). Alternatively, the blocking group may be attached at both the 3' and 2' positions and may be cleaved to expose the 3'OH group.

Suitable blocking groups will be apparent to the skilled person and may be formed from any suitable protecting group disclosed in "Protective Groups in Organic Synthesis", T. W. Greene and P. G. M. Wuts, 3rd Ed., Wiley Interscience, New York, which is hereby incorporated herein by reference in its entirety to the extent that it does not conflict with the present disclosure. The blocking group is preferably removable (or modifiable) to produce a 3' OH group. The process used to obtain the 3' OH group may be any suitable chemical or enzymic reaction.

Blocking moieties may be as described in U.S. Pat. No. 7,414,116, which is hereby incorporated herein by reference in its entirety to the extent that it does not conflict with the present disclosure Regardless of how the blocking moiety is removed, the wash composition comprises a scavenger compound that inhibits interaction of reactive compounds used in or resulting from the deblocking step with polynucleotides used in or generated from the sequencing process, enzymes used in the sequencing process, or other reagents used in the sequencing process. Accordingly, the presence of the scavenger compounds may reduce damage to the polynucleotides, enzymes, or other reagents, which may allow for additional cycles of sequencing to be performed relative to sequencing processes that do not include the scavenger compound in the wash composition.

The wash composition may include any suitable scavenger compound, which may depend on the reagents used in the deblocking step or reaction products resulting from the deblocking step.

As used herein, a "scavenger compound" is a compound that inhibits interaction of reactive compounds used in or resulting from the deblocking step with polynucleotides used in or generated from the sequencing process, enzymes used the sequencing process, or other reagents or compounds used in the sequencing process. In some embodiments, a scavenger compound is a compound that oxidizes a cleavage agent that is a reducing agent under conditions of the sequencing procedure. Preferably, the scavenger compound is capable of oxidizing a phosphine at room temperature in 50 mM tris(hydroxymethyl)aminomethane (Tris) buffer to 1 M Tris buffer. For example, the scavenger compound may oxidize tris(hydroxymethyl)phosphine to tris(hydroxymethyl)phosphine oxide at room temperature in 50 mM Tris buffer to 1 M Tris buffer.

Any suitable scavenger compound may be included in the wash composition. Examples of scavenger compounds that may oxidize reducing agents include compounds comprising a disulfide moiety or an azide moiety. Preferably, the scavenger comprises a a disulfide moiety. In some examples, the scavenger compound is selected from the group consisting of cystine, lipoic acid, 3,3'-dithiodipropionic acid (DPPA), and a pegylated azide, such as a compound according to Formula I below:

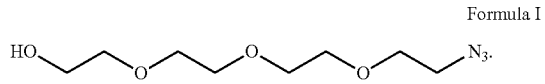 [SMILES: [N-]=[N+]=NCCOCCOCCOCCO]

Formula I

A particularly preferred scavenger compound is DPPA.

The scavenger compounds may be present in the wash composition at any suitable concentration. For example, the scavenger compound may be present in the wash composition at a concentration from about 0.1 mM to about 50 mM, such as from about 0.5 mM to about 20 mM, or from about 1 mM to about 10 mM.

The wash composition may include any other suitable components. Preferably, the wash composition comprises a buffer compatible with subsequent step of the sequencing procedure; e.g., incorporation of the next blocked, labeled nucleotide in the sequence.

For example, the wash composition comprising the scavenger may comprise a buffer, such as Tris buffer. The buffer may be present at any suitable concentration. For example, the buffer may be present at a concentration from about 5 mM to about 2 M such as from about 10 mm to about 1.5 M, or from about 50 mM to about 1M. In some preferred embodiments, the wash composition comprises a Tris buffer at a concentration from about 75 mM to about 250 mM, such from about 100 mM to about 200 mM, or about 150 mM.

The wash composition comprising the scavenger may comprise a detergent. Any suitable detergent may be included in the wash composition. For example, the wash composition may comprise an anionic, cationic, zwitterionic or nonionic detergent. In some preferred embodiments, the wash composition comprises a nonionic detergent. An example of a suitable nonionic detergent is Tween 20 (available from ThermoFischer Scientific). The detergent may be present in the wash composition at any suitable concentration. For example, the detergent may be present in the wash composition from about 0.01% by weight to about 0.5% by weight, such as from about 0.02% by weight to about 0.1% by weight, or from about 0.03% by weight to about 0.07% by weight. In some preferred embodiments, the wash composition comprises Tween 20 at a concentration from about 0.03% by weight to about 0.07% by weight, or about 0.5% by weight.

The wash composition comprising the scavenger may comprise a chelating agent. Any suitable chelating agent may be included in the wash composition. For example, the wash composition may comprise dihydroxyethylglycine (HEG) or ethylenediaminetetraacetic acid (EDTA). The chelating agent may be present in any suitable concentration. For example, the chelating agent may be present in the wash composition at a concentration from about 0.1 mM to about 50 mM, such as from about 0.5 mM to about 20 mM. In some preferred embodiments, the wash composition comprises HEG at a concentration from about 5 mM to about 15 mM, such as about 10 mM.

The wash composition comprising the scavenger may comprise a salt. For example, the wash composition may comprise sodium chloride. The salt may be present in the wash composition at any suitable concentration. For example, the salt may be present at a concentration from about 10 mM to about 250 mM, such as from about 25 mM to about 100 mM, from about 30 mM to about 70 mM, or about 50 mM.

It will be understood that the wash composition comprising the scavenger compound may be incubated with the target and copy strands for a period of time rather than continuously flowing the wash composition passed the target and copy strands. Of course, the wash composition comprising the scavenger may be continuously flowed passed the target and copy strands following deblocking.

In some embodiments, the wash composition comprising the scavenger is used for both the post cleavage (deblocking) wash and the detection wash. In such embodiments, the wash composition preferably further comprises an antioxidant to prevent photo-induced damage. The composition may comprise any suitable amount of an antioxidant. For example, the composition may comprise one or more antioxidant in a combined total antioxidant concentration from about 2 mM to about 50 mM, such as from about 5 mM to about 40 mM, or from about 15 mM to about 25 mM, or about 20 mM. Suitable antioxidants include ascorbate, acetovanillone, and 6-hydroxy-2,5,7,8-tetramethylchroman-2-carboxylic acid (Trolox). In some preferred embodiments, the wash composition comprises sodium ascorbate.

When the same composition is used for the post-cleave (deblocking) wash and in the scanning (detection) step, the number of compositions used in the sequencing process may be reduced, which may provide one or more advantage. For example, reducing the number of reagents or compositions may reduce the burden of ensuring good manufacturing practices and composition or reagent stability. The cartridge size and complexity of sequencing instrument may be reduced. There may be fewer failure modes, and there may be savings in the cost of goods. These and other advantages will be evident to those of skill in the polynucleotide sequencing arts.

In some embodiments, a composition suitable for post-cleave wash and scanning comprises a buffer, an antioxidant, a detergent, and a chelator. For example, the composition may include components as described in Table 1 below:

| REAGENT | CONCENTRATION |
| --- | --- |
| Buffer | 50 mM to 1M |
| Antioxidant | 2 mM to 50 mM |
| Chelator | 0.5 mM to 20 mM |
| Detergent | 0.01% to 0.2% by weight |
| Scavenger | 1 mM to 20 mM |

A more specific example of some components of a composition suitable for post-cleave wash and scanning is provided in Table 2 below:

| REAGENT | CONCENTRATION |
| --- | --- |
| Tris buffer | 50 mM to 1M |
| Sodium ascorbate | 2 mM to 50 mM |
| HEG | 0.5 mM to 20 mM |
| Tween 20 | 0.01% to 0.2% by weight |
| Lipoic acid or DPPA | 1 mM to 20 mM |

An even more specific example of some components of a composition suitable for post-cleave wash and scanning is provided in Table 3 below:

| REAGENT | CONCENTRATION |
| --- | --- |
| Tris buffer | 50 mM to 1M |
| Sodium ascorbate | 20 mM |
| HEG | 10 mM |
| Tween 20 | 0.05% by weight |
| Lipoic acid or DPPA | 10 mM |

As discussed throughout, provided are improved methods for sequencing polynucleotides. Exemplary sequencing methods are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference. One useful method for high throughput or rapid sequencing is sequencing by synthesis (SBS). SBS techniques include, but are not limited to, the Genome Analyzer systems (Illumina Inc., San Diego, Calif.) and the True Single Molecule Sequencing (tSMS)™ systems (Helicos BioSciences Corporation, Cambridge, Mass.). Briefly, a number of sequencing by synthesis reactions are used to elucidate the identity of a plurality of bases at target positions within a target sequence. All these reactions rely on the use of a target nucleic acid sequence having at least two domains; a first domain to which a sequencing primer will hybridize, and an adjacent second domain, for which sequence information is desired. Upon formation of an assay complex, extension enzymes are used to add deoxynucleotide triphosphates (dNTPs) to a sequencing primer that is hybridized to first domain, and each addition of dNTPs is read to determine the identity of the added dNTP. This may proceed for many cycles. SBS techniques such as, the Genome Analyzer systems (Illumina Inc., San Diego, Calif.) and the True Single Molecule Sequencing (tSMS)™ systems (Helicos BioSciences Corporation, Cambridge, Mass.), utilize labeled nucleotides to determine the sequence of a target nucleic acid molecule. A target nucleic acid molecule can be hybridized with a primer and incubated in the presence of a polymerase and a labeled nucleotide containing a blocking group. The primer is extended such that the nucleotide is incorporated. The presence of the blocking group permits only one round of incorporation, that is, the incorporation of a single nucleotide. The presence of the label permits identification of the incorporated nucleotide. A plurality of homogenous single nucleotide bases can be added during each cycle, such as used in the True Single Molecule Sequencing (tSMS)™ systems (Helicos BioSciences Corporation, Cambridge, Mass.) or, alternatively, all four nucleotide bases can be added during each cycle simultaneously, such as used in the Genome Analyzer systems (Illumina Inc., San Diego, Calif.), particularly when each base is associated with a distinguishable label. After identifying the incorporated nucleotide by its corresponding label, both the label and the blocking group can be removed, thereby allowing a subsequent round of incorporation and identification. Determining the identity of the added nucleotide base includes, in some embodiments, repeated exposure of the newly added labeled bases a light source that can induce a detectable emission due the addition of a specific nucleotide base, i.e. dATP, dCTP, dGTP or dTTP. The methods and compositions disclosed herein are particularly useful for such SBS techniques. In addition, the methods and compositions described herein may be particularly useful for sequencing from an array of nucleic acids, where multiple sequences can be read simultaneously from multiple positions on the array since each nucleotide at each position can be identified based on its identifiable label. Exemplary methods are described in US 2009/0088327; US 2010/0028885; and US 2009/0325172, each of which is incorporated herein by reference.

Referring now to FIGS. 1-3, overviews of some steps in SBS processes are shown. The compositions employed at different stages of the SBS process are shown. As shown in FIG. 1, the compositions include an incorporation composition (Inc.), a scan composition (Scan), a de-blocking composition (De-Block), and a post cleave wash composition (PCW). The incorporation composition (Inc.) comprises blocked, labeled nucleotides and may include a chain extending enzyme. The blocked, labeled nucleotides are incubated with the template strands and a chain extending enzyme in an incorporation step to incorporate an appropriate nucleotide into a copy strand based on the sequence of the template strand.

Following the incorporation step, the unincorporated blocked, labeled nucleotides may be washed away and the identity of the nucleotide incorporated into the copy strand can be determined. A scan composition (Scan) is present during detection of the identity of the incorporated blocked, labeled nucleotide. The scan composition comprises an antioxidant to protect the template strand and the copy strand from damage that may be induced by light during the detection step. See, e.g., U.S. Pat. Nos. 9,115,353 and 9,217,178, which are hereby incorporated herein by reference in their respective entireties to the extent that they do not conflict with the present disclosure. A universal wash composition (not shown) may be employed to wash away the unincorporated blocked, labeled nucleotides prior to introduction of the scan composition or the introduction of the scan composition may serve to wash away the unincorporated blocked, labeled nucleotides.

Following the detection step, the blocking moiety and the labeled moiety may be removed from the nucleotide incorporated into the copy strand by introducing a de-blocking composition (De-Block) that comprises a cleavage agent. Preferably, cleavage agent removes both the blocking moiety and the labeled moiety. For example, the labeled moiety may serve as the blocking moiety, the labeled moiety may be on the blocking moiety, the labeled moiety may be attached to the nucleotide by the same linker as the blocking moiety, etc.

After the de-blocking step, the removed blocking moiety and cleavage agent are washed away with a wash composition (PC Wash), and the process may be repeated. The PCW wash composition may include a scavenger (Scav Wash) as shown in FIG. 2. The Scav Wash may be incubated in the environment of the template strand and the copy strand for a period of time to enable the scavenger to interact with one or more reactive compounds resulting from the deblocking step or the Scav Wash may be continuously washed through the environment of the template strand and the copy strand. The post-cleave wash step may also include one or more washes with a universal buffer in addition to the Scav Wash.

As shown in FIG. 3, a single composition, ScavScan, may be employed for both the scanning (detection) step and the PCW step. The ScavScan composition includes an antioxidant to reduce potential photo-induced damage during the scanning step and includes a scavenger to interact with reactive compounds in or resulting from the de-blocking step.

The PCW wash step, including any washes with universal wash buffer or another composition that does not include a scavenger, may be of any suitable length of time. The use of a scavenger should enable shorter overall PCW wash step times relative to sequencing processes that do not include a scavenger in the wash, because the presence of the scavenger should diminish the impact of reactive products from the deblocking step with less wash volume.

The total PCW wash step, the time following the de-blocking step to the time in which the incorporate step begins, may be of any suitable length of time. The amount of time for the PCW wash step may vary depending on the sequencing instrument and platform used. In some examples, the total time for the PCW wash step may be from about 1 seconds to about 120 seconds, such as from about 1 second to about 90 seconds, from about 1 second to about 20 seconds, from about 5 seconds to 60 seconds, or the like.

In some embodiments, the PCW wash step includes a step in which a wash composition comprising a scavenger is contacted with the template strand and the copy strand and includes a step in which a wash composition that does not include a scavenger, such as a universal wash buffer, is flowed passed the template strand and the copy strand. The wash step with the scavenger and the wash step without the scavenger may take any suitable relative amount of time.

In some embodiments, the PCW wash step employs more than one wash with a composition that does not include a scavenger. For example, a first component of the PCW wash may be a first wash with a composition that does not include a scavenger, a second wash with a composition that includes a scavenger, and a third was with a composition that does not include a scavenger.

In some embodiments, the PCW wash step employs a wash with a composition that does not include a scavenger and a wash with a composition that does include a scavenger. For example, a first component of the PCW wash may be a first wash with a composition that does not include a scavenger, and a second wash with a composition that includes a scavenger. By way of another example, a first component of the PCW wash may be a first wash with a composition that includes a scavenger, and a second wash with a composition that does not include a scavenger.

Any suitable total volume of wash compositions may be employed in the PCW was step.

The total volume employed may depend on the sequencing instrument and platform employed. In some embodiments, the total volume of wash composition is from about 100 microliters to about 1000 microliters, such as from about 200 microliters to about 900 microliters.

The use of a scavenger in the PCW wash should enable longer runs, as damage to the polynucleotides, enzymes, and other reagents should be reduced relative to sequencing processes that do not include a scavenger in the wash. Of course, the sequencing processes employing a scavenger in the PCW wash may include any suitable number of cycles of incorporation, detection, and de-blocking. Thus, the methods described herein include, but are not limited to, from about 50 cycles to about 1,000 cycles, such as from about 100 cycles to about 500 cycles, or from about 100 cycles to about 300 cycles.

Figure 4:
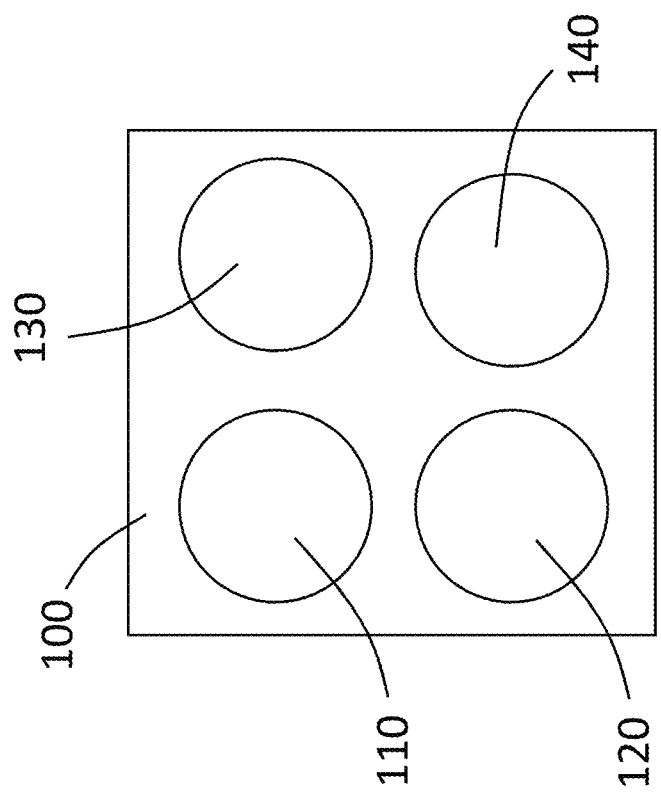
FIG. 4 is a schematic top plan view of a cartridge including compositions for sequencing in accordance with various embodiments disclosed herein.

In some embodiments, cartridges for use with sequencing instruments may include a chamber from which a composition comprising an antioxidant and a scavenger may be withdrawn or expelled for use in a scanning step and a post-cleave wash step. For example and with reference to FIG. 4, a cartridge 100 comprising a plurality of chambers 110, 120, 130, 140 is shown. Each chamber 110, 120, 130, 140 contains a single composition. A composition comprising reagents for incorporating a blocked, labeled nucleotide into a copy polynucleotide strand complementary to at least a portion of a template polynucleotide strand is disposed in the first chamber 110. A composition comprising an antioxidant and a scavenger is disposed in the second chamber 120. The composition disposed in the second chamber 120 may be used for both the scanning (detection) step and the post-cleave wash step. A composition comprising reagents for chemically removing a label and blocking moiety from the blocked, labeled nucleotide incorporated into the copy strand is disposed in the third chamber 130. A universal wash buffer is disposed in the fourth chamber 140.

The sequencing methods described herein may be performed in any suitable manner, using any suitable equipment. In some embodiments, the sequencing methods employ a solid support on which the multiple template polynucleotide strands are immobilized. The term immobilized as used herein is intended to encompass direct or indirect attachment to a solid support via covalent or non-covalent bond(s). In particular embodiments, all that is required is that the polynucleotides remain immobilized or attached to a support under conditions in which it is intended to use the support, for example in applications requiring nucleic acid amplification and/or sequencing. For example, oligonucleotides or primers may be immobilized such that a 3' end is available for enzymatic extension and/or at least a portion of the sequence is capable of hybridizing to a complementary sequence. Immobilization can occur via hybridization to a surface attached primer, in which case the immobilized primer or oligonucleotide may be in the 3'-5' orientation. Alternatively, immobilization may occur by non-base-pairing hybridization, such as the covalent attachment.

By way of example, the polynucleotides may be attached to the surface by hybridization or annealing to one or more primers in a patch of primers. Hybridization may be accomplished, for example, by ligating an adapter to the ends of the template polynucleotides. The nucleic acid sequence of the adapter can be complementary to the nucleic acid sequence of the primer, thus, allowing the adapter to bind or hybridize to the primer on the surface. Optionally, the polynucleotides may be single- or double-stranded and adapters may be added to the 5' and/or 3' ends of the polynucleotides. Optionally, the polynucleotides may be double-stranded, and adapters may be ligated onto the 3' ends of double-stranded polynucleotide. Optionally, polynucleotides may be used without any adapter. In some embodiments, template polynucleotides may be attached to a surface by interactions other than hybridization to a complementary primer. For example, a polynucleotide may be covalently attached to a surface using a chemical linkage such as those resulting from click chemistry or a receptor-ligand interaction such as streptavidin-biotin binding.

Primer oligonucleotides, oligonucleotide primers and primers are used throughout interchangeably and are polynucleotide sequences that are capable of annealing specifically to one or more polynucleotide templates to be amplified or sequenced. Generally, primer oligonucleotides are single-stranded or partially single-stranded. Primers may also contain a mixture of non-natural bases, non-nucleotide chemical modifications or non-natural backbone linkages so long as the non-natural entities do not interfere with the function of the primer. Optionally, a patch of primers on a surface of a solid support may comprise one or more different pluralities of primer molecules. By way of example, a patch may comprise a first, second, third, fourth, or more pluralities of primer molecules each plurality having a different sequence. It will be understood that for embodiments having different pluralities of primers in a single patch, the different pluralities of primers may share a common sequence so long as there is a sequence difference between at least a portion of the different pluralities. For example, a first plurality of primers may share a sequence with a second plurality of primers as long the primers in one plurality have a different sequence not found in the primers of the other plurality.

The template polynucleotides may be amplified on the surface of the solid support. Polynucleotide amplification includes the process of amplifying or increasing the numbers of a polynucleotide template and/or of a complement thereof that are present, by producing one or more copies of the template and/or or its complement. Amplification may be carried out by a variety of known methods under conditions including, but not limited to, thermocycling amplification or isothermal amplification. For example, methods for carrying out amplification are described in U.S. Publication No. 2009/0226975; WO 98/44151; WO 00/18957; WO 02/46456; WO 06/064199; and WO 07/010251; which are incorporated by reference herein in their entireties. Briefly, in the provided methods, amplification can occur on the surface to which the polynucleotide molecules are attached. This type of amplification can be referred to as solid phase amplification, which when used in reference to polynucleotides, refers to any polynucleotide amplification reaction carried out on or in association with a surface (e.g., a solid support). Typically, all or a portion of the amplified products are synthesized by extension of an immobilized primer. Solid phase amplification reactions are analogous to standard solution phase amplifications except that at least one of the amplification primers is immobilized on a surface (e.g., a solid support).

Suitable conditions include providing appropriate buffers/solutions for amplifying polynucleotides. Such solutions include, for example, an enzyme with polymerase activity, nucleotide triphosphates, and, optionally, additives such as DMSO or betaine. Optionally, amplification is carried out in the presence of a recombinase agent as described in U.S. Pat. No. 7,485,428, which is incorporated by reference herein in its entirety, which allows for amplification without thermal melting. Briefly, recombinase agents such as the RecA protein from *E. coli* (or a RecA relative from other phyla), in the presence of, for example, ATP, dATP, ddATP, UTP, or ATPγS, will form a nucleoprotein filament around single-stranded DNA (e.g., a primer). When this complex comes in contact with homologous sequences the recombinase agent will catalyze a strand invasion reaction and pairing of the primer with the homologous strand of the target DNA. The original pairing strand is displaced by strand invasion leaving a bubble of single stranded DNA in the region, which serves as a template for amplification.

Solid-phase amplification may comprise a polynucleotide amplification reaction comprising only one species of oligonucleotide primer immobilized to a surface.

Alternatively, the surface may comprise a plurality of first and second different immobilized oligonucleotide primer species. Solid phase nucleic acid amplification reactions generally comprise at least one of two different types of nucleic acid amplification, interfacial and surface (or bridge) amplification. For instance, in interfacial amplification the solid support comprises a template polynucleotide that is indirectly immobilized to the solid support by hybridization to an immobilized oligonucleotide primer, the immobilized primer may be extended in the course of a polymerase-catalyzed, template-directed elongation reaction (e.g., primer extension) to generate an immobilized polynucleotide that remains attached to the solid support. After the extension phase, the polynucleotides (e.g., template and its complementary product) are denatured such that the template polynucleotide is released into solution and made available for hybridization to another immobilized oligonucleotide primer. The template polynucleotide may be made available in 1, 2, 3, 4, 5 or more rounds of primer extension or may be washed out of the reaction after 1, 2, 3, 4, 5 or more rounds of primer extension.

In surface (or bridge) amplification, an immobilized polynucleotide hybridizes to an immobilized oligonucleotide primer. The 3' end of the immobilized polynucleotide provides the template for a polymerase-catalyzed, template-directed elongation reaction (e.g., primer extension) extending from the immobilized oligonucleotide primer. The resulting double-stranded product "bridges" the two primers and both strands are covalently attached to the support. In the next cycle, following denaturation that yields a pair of single strands (the immobilized template and the extended-primer product) immobilized to the solid support, both immobilized strands can serve as templates for new primer extension.

Amplification may be used to produce colonies of immobilized polynucleotides. For example, the methods can produce clustered arrays of polynucleotide colonies, analogous to those described in U.S. Pat. No. 7,115,400; U.S. Publication No. 2005/0100900; WO 00/18957; and WO 98/44151, which are incorporated by reference herein in their entireties. "Clusters" and "colonies" are used interchangeably and refer to a plurality of copies of a polynucleotide having the same sequence and/or complements thereof attached to a surface. Typically, the cluster comprises a plurality of copies of a polynucleotide having the same sequence and/or complements thereof, attached via their 5' termini to the surface. The copies polynucleotides making up the clusters may be in a single or double stranded form.

Thus, the plurality of template polynucleotides may be in a cluster, each cluster containing template polynucleotides of the same sequence. A plurality of clusters can be sequenced, each cluster comprising polynucleotides of the same sequence. Optionally, the sequence of the polynucleotides in a first cluster is different from the sequence of the nucleic acid molecules of a second cluster. Optionally, the cluster is formed by annealing to a primer on a solid surface a template polynucleotide and amplifying the template polynucleotide under conditions to form the cluster comprising the plurality of template polynucleotides of the same sequence. Amplification can be thermal or isothermal.

Each colony may comprise polynucleotides of the same sequences. In particular embodiments, the sequence of the polynucleotides of one colony is different from the sequence of the polynucleotides of another colony. Thus, each colony comprises polynucleotides having different nucleic acid sequences. All the immobilized polynucleotides in a colony are typically produced by amplification of the same polynucleotide. In some embodiments, it is possible that a colony of immobilized polynucleotides contains one or more primers without an immobilized polynucleotide to which another polynucleotide of different sequence may bind upon additional application of solutions containing free or unbound polynucleotides. However, due to the lack of sufficient numbers of free primers in a colony, this second or invading polynucleotide may not amplify to significant numbers. The second or invading polynucleotide typically is less than 1, 0.5, 0.25, 0.1, 0.001 or 0.0001% of the total population of polynucleotides in a single colony. Thus, the second or invading polynucleotide may not be optically detected or detection of the second or invading polynucleotide is considered background noise or does not interfere with detection of the original, immobilized polynucleotides in the colony. In such embodiments, the colony will be apparently homogeneous or uniform in accordance with the resolution of the methods or apparatus used to detect the colony.

The clusters may have different shapes, sizes and densities depending on the conditions used. For example, clusters may have a shape that is substantially round, multi-sided, donut-shaped or ring-shaped. The diameter or maximum cross section of a cluster may be from about 0.2 µm to about 6 µm, about 0.3 µm to about 4 µm, about 0.4 µm to about 3 µm, about 0.5 µm to about 2 µm, about 0.75 µm to about 1.5 µm, or any intervening diameter. Optionally, the diameter or maximum cross section of a cluster may be at least about 0.5 µm, at least about 1 µm, at least about 1.5 µm, at least about 2 µm, at least about 2.5 µm, at least about 3 µm, at least about 4 µm, at least about 5 µm, or at least about 6 µm. The diameter of a cluster may be influenced by a number of parameters including, but not limited to, the number of amplification cycles performed in producing the cluster, the length of the polynucleotide template, the GC content of the polynucleotide template, the shape of a patch to which the primers are attached, or the density of primers attached to the surface upon which clusters are formed. However, as discussed above, in all cases, the diameter of a cluster may be no larger than the patch upon which the cluster is formed. For example, if a patch is a bead, the cluster size will be no larger than the surface area of the bead. The density of clusters can be in the range of at least about $0.1/mm^2$, at least about $1/mm^2$, at least about $10/mm^2$, at least about $100/mm^2$, at least about $1,000/mm^2$, at least about $10,000/mm^2$ to at least about $100,000/mm^2$. Optionally, the clusters have a density of, for example, $100,000/mm^2$ to $1,000,000/mm^2$ or $1,000,000/mm^2$ to $10,000,000/mm^2$. The methods provided herein can produce colonies that are of approximately equal size. This occurs regardless of the differences in efficiencies of amplification of the polynucleotides of different sequence.

Clusters may be detected, for example, using a suitable imaging means, such as, a confocal imaging device or a charge coupled device (CCD) or CMOS camera. Exemplary imaging devices include, but are not limited to, those described in U.S. Pat. Nos. 7,329,860; 5,754,291; and 5,981,956; and WO 2007/123744, each of which is herein incorporated by reference in its entirety. The imaging apparatus may be used to determine a reference position in a cluster or in a plurality of clusters on the surface, such as the location, boundary, diameter, area, shape, overlap and/or center of one or a plurality of clusters (and/or of a detectable signal originating therefrom). Such a reference position may be recorded, documented, annotated, converted into an interpretable signal, or the like, to yield meaningful information.

As used herein the term support refers to a substrate for attaching polynucleotides. A support is a material having a rigid or semi-rigid surface to which a polynucleotide can be attached or upon which nucleic acids can be synthesized and/or modified. Supports can include any resin, gel, bead, well, column, chip, flowcell, membrane, matrix, plate, filter, glass, controlled pore glass (CPG), polymer support, membrane, paper, plastic, plastic tube or tablet, plastic bead, glass bead, slide, ceramic, silicon chip, multi-well plate, nylon membrane, fiber optic, and PVDF membrane.

A support may include any flat wafer-like substrates and flat substrates having wells, such as a microtiter plate, including 96-well plates. Exemplary flat substrates include chips, slides, etched substrates, microtiter plates, and flow cell reactors, including multi-lane flow cell reactors having multiple microfluidic channels, such as the eight-channel flow cell used in the cBot sequencing workstation (Illumina, Inc., San Diego, Calif.). Exemplary flow cells are described in WO 2007/123744, which is incorporated herein by reference in its entirety. Optionally, the flowcell is a patterned flowcell. Suitable patterned flowcells include, but are not limited to, flowcells described in WO 2008/157640, which is incorporated by reference herein in its entirety.

A support may also include beads, including magnetic beads, hollow beads, and solid beads. Beads may be used in conjunction with flat supports, such flat supports optionally also containing wells. Beads, or alternatively microspheres, refer generally to a small body made of a rigid or semi-rigid material. The body may have a shape characterized, for example, as a sphere, oval, microsphere, or other recognized particle shape whether having regular or irregular dimensions. The sizes of beads, in particular, include, without limitation, about 1 µm, about 2 µm, about 3 µm, about 5 µm, about 10 µm, about 20 µm, about 30 µm, about 40 µm, about 60 µm, about 100 µm, about 150 µm or about 200 µm in diameter. Other particles may be used in ways similar to those described herein for beads and microspheres.

The composition of a support may vary depending, for example, on the format, chemistry and/or method of attachment and/or on the method of nucleic acid synthesis. Support materials that can be used in accordance with the present disclosure include, but are not limited to, polypropylene, polyethylene, polybutylene, polyurethanes, nylon, metals, and other suitable materials. Exemplary compositions include supports, and chemical functionalities imparted thereto, used in polypeptide, polynucleotide and/or organic moiety synthesis. Such compositions include, for example, plastics, ceramics, glass, polystyrene, melamine, methylstyrene, acrylic polymers, paramagnetic materials, thoria sol, carbon graphite, titanium dioxide, latex or cross-linked dextrans such as Sepharose™, cellulose, nylon, cross-linked micelles and Teflon™, as well as any other materials which can be found described in, for example, "*Microsphere Detection Guide*" from Bangs Laboratories, Fishers Ind., which is incorporated herein by reference. A support particle may be made of cross-linked starch, dextrans, cellulose, proteins, organic polymers including styrene polymers including polystyrene and methylstyrene as well as other styrene co-polymers, plastics, glass, ceramics, acrylic polymers, magnetically responsive materials, colloids, thoriasol, carbon graphite, titanium dioxide, nylon, latex, or TEFLON®. "Microsphere Detection Guide" from Bangs Laboratories, Fishers, Inc., hereby incorporated by reference in its entirety, is a helpful guide. Further exemplary supports within the scope of the present disclosure include, for example, those described in US Application Publication No. 02/0102578 and U.S. Pat. No. 6,429,027, both of which are incorporated herein by reference in their entirety.

For example, and with reference to FIG. 5, an embodiment of a solid support 200, such as a flow cell, is shown. The solid support 200 has a surface 210 to which clusters 300 containing multiple template polynucleotide strands having the same nucleotide sequence are bound to the surface 210 of the solid support 210. The surface 210 of the solid support 200 may be planar.

Fluid compositions containing reagents, wash buffers, and the like may flow over the surface 210 of the solid support 200 to interact with the template polynucleotides in the clusters 300. The flow of the compositions may occur in any direction, such as the direction indicated by the arrows in FIG. 5.

Sequencing apparatus with which the flow cell 300 may be used may be configured to flow reagents and compositions across the surface 210 to interact with the template strands in the clusters 300. For example, the apparatus may cause chain extending enzymes, sequencing primers, nucleotides, wash compositions, unblocking reagents, post cleave wash compositions, and the like to flow across the surface 210 of the solid support 200, such as a flow cell, to interact with the template polynucleotides in the clusters 300 at the appropriate times to carry out sequencing of the template strands.

Each cluster 300 may contain the same template polynucleotides or different polynucleotides than another cluster 300.

The template polynucleotides to be sequenced may be obtained from any biological sample using known, routine methods. Suitable biological samples include, but are not limited to, a blood sample, biopsy specimen, tissue explant, organ culture, biological fluid or any other tissue or cell preparation, or fraction or derivative thereof or isolated therefrom. The biological sample can be a primary cell culture or culture adapted cell line including but not limited to genetically engineered cell lines that may contain chromosomally integrated or episomal recombinant nucleic acid sequences, immortalized or immortalizable cell lines, somatic cell hybrid cell lines, differentiated or differentiatable cell lines, transformed cell lines, stem cells, germ cells (e.g. sperm, oocytes), transformed cell lines and the like. For example, polynucleotide molecules may be obtained from primary cells, cell lines, freshly isolated cells or tissues, frozen cells or tissues, paraffin embedded cells or tissues, fixed cells or tissues, and/or laser dissected cells or tissues. Biological samples can be obtained from any subject or biological source including, for example, human or non-human animals, including mammals and non-mammals, vertebrates and invertebrates, and may also be any multi-cellular organism or single-celled organism such as a eukaryotic (including plants and algae) or prokaryotic organism, archaeon, microorganisms (e.g. bacteria, archaea, fungi, protists, viruses), and aquatic plankton.

Once the polynucleotides are obtained, a plurality of polynucleotides molecules of different sequence for use in the provided methods may be prepared using a variety of standard techniques available and known. Exemplary methods of polynucleotide molecule preparation include, but are not limited to, those described in Bentley et al., *Nature* 456:49-51 (2008); U.S. Pat. No. 7,115,400; and U.S. Patent Application Publication Nos. 2007/0128624; 2009/0226975; 2005/0100900; 2005/0059048; 2007/0110638; and 2007/0128624, each of which is herein incorporated by reference in its entirety. The template polynucleotides may contain a variety of sequences including, but not limited to, universal sequences and known or unknown sequences. For example, polynucleotide may comprise one or more regions of known sequence (e.g., an adaptor) located on the 5' and/or 3' ends. Such template polynucleotides may be formed by attaching adapters to the ends of a polynucleotides of unknown sequence. When the polynucleotides comprise known sequences on the 5' and 3' ends, the known sequences may be the same or different sequences. Optionally, a known sequence located on the 5' and/or 3' ends of the polynucleotides is capable of hybridizing to one or more primers immobilized on the surface. For example, a polynucleotide comprising a 5' known sequence may hybridize to a first plurality of primers while the 3' known sequence may hybridize to a second plurality of primers. Optionally, polynucleotides comprise one or more detectable labels. The one or more detectable labels may be attached to the polynucleotide template at the 5' end, at the 3' end, and/or at any nucleotide position within the polynucleotide molecule. The polynucleotides for use in the provided methods may comprise the polynucleotide to be amplified and/or sequenced and, optionally, short nucleic acid sequences at the 5' and/or 3' end(s).

A short nucleic acid sequence that is added to the 5' and/or 3' end of a polynucleotide may be a universal sequence. A universal sequence is a region of nucleotide sequence that is common to, i.e., shared by, two or more polynucleotides, where the two or more polynucleotides also have regions of sequence differences. A universal sequence that may be present in different members of a plurality of polynucleotides may allow the replication or amplification of multiple different sequences using a single universal primer that is complementary to the universal sequence. Similarly, at least one, two (e.g., a pair) or more universal sequences that may be present in different members of a collection of polynucleotides may allow the replication or amplification of multiple different sequences using at least one, two (e.g., a pair) or more single universal primers that are complementary to the universal sequences. Thus, a universal primer includes a sequence that may hybridize specifically to such a universal sequence. The polynucleotide may be modified to attach universal adapters (e.g., non-target nucleic acid sequences) to one or both ends of the different target sequences, the adapters providing sites for hybridization of universal primers. This approach has the advantage that it is not necessary to design a specific pair of primers for each polynucleotide to be generated, amplified, sequenced, and/or otherwise analyzed; a single pair of primers can be used for amplification of different polynucleotides provided that each polynucleotide is modified by addition of the same universal primer-binding sequences to its 5' and 3' ends.

The polynucleotides may also be modified to include any nucleic acid sequence desirable using standard, known methods. Such additional sequences may include, for example, restriction enzyme sites, or indexing tags in order to permit identification of amplification products of a given nucleic acid sequence.

As used herein, the term different when used in reference to two or more polynucleotides means that the two or more polynucleotides have nucleotide sequences that are not the same. For example, two polynucleotides can differ in the content and order of nucleotides in the sequence of one polynucleotide compared to the other polynucleotide. The term can be used to describe polynucleotides whether they are referred to as copies, amplicons, templates, targets, primers, oligonucleotides, or the like.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation may not be explicitly disclosed, each is specifically contemplated and described herein. For example, if a method is disclosed and discussed and a number of modifications that can be made to the method steps are discussed, each and every combination and permutation of the method steps, and the modifications that are possible are specifically contemplated unless specifically indicated to the contrary.

Likewise, any subset or combination of these is also specifically contemplated and disclosed. This concept applies to all aspects of this disclosure. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

EXAMPLES

Current sequencing protocols for Illumina, Inc.'s 2-channel platform include the use of an incorporation composition, a scan composition, a deblocking composition, and a universal wash composition. The incorporation composition comprises blocked, labeled nucleotides, the scan composition comprises an anti-oxidant, and the deblocking composition comprises a cleavage agent. The universal wash composition is used following deblocking in as step referred to as a post-cleave wash ("PCW"). In some instances, lipoic acid is included as a scavenger. The universal wash composition may also be employed between other steps (in addition to between deblocking and incorporation). For example, the universal wash composition may be employed between the incorporation step and the scanning (detection) step or between the scanning step and the deblocking step.

To test the effects of a scavenger in the PCW and in an attempt to reduce the number of reagents employed in the sequencing process, the following compositions were employed: BB2 (Universal wash composition with 50 mM Tris buffer); BB7 (BB2+ lipoic acid), BB2+ (Universal wash composition with 150 mM Tris buffer); Scan Mix (VSM); ScavScan (VSM+lipoic acid).

The composition of VSM, ScavScan, BB2, BB7, and BB2+ are presented in Tables 4-8 below.

TABLE 4

VSM

| Component | Concentration |
|---|---|
| Tris buffer | 1M |
| NaAscorbate | 20 mM |
| Dihydroxyethylglycine (HEG) | 10 mM |
| Tween 20 | 0.05% by weight |

TABLE 5

ScavScan

| Component | Concentration |
|---|---|
| Tris buffer | 1M |
| NaAscorbate | 20 mM |
| Dihydroxyethylglycine (HEG) | 10 mM |
| Tween 20 | 0.05% by weight |
| Lipoic Acid | 10 mM |

TABLE 6

BB2

| Component | Concentration |
|---|---|
| Tris buffer | 50 mM |
| NaCl | 50 mM |
| Ethylenediaminetetraacetic acid (EDTA) | 10 mM |
| Tween 20 | 0.05% by weight |

TABLE 7

BB7

| Component | Concentration |
|---|---|
| Tris buffer | 50 mM |
| NaCl | 50 mM |
| Ethylenediaminetetraacetic acid (EDTA) | 10 mM |
| Tween 20 | 0.05% by weight |
| Lipoic Acid | 10 mM |

TABLE 8

| BB2+ | |
| --- | --- |
| Component | Concentration |
| Tris buffer | 150 mM |
| NaCl | 50 mM |
| Ethylenediaminetetraacetic acid (EDTA) | 10 mM |
| Tween 20 | 0.05% by weight |

The addition of lipoic acid (a scavenger) to the universal wash composition, in a composition referred to as "BB7," reduces phasing and reduces wash volume relative to universal wash composition alone. Reduced phasing may enable longer sequencing runs (more cycles). Reduced wash volume may enable faster sequencing times.

To test whether the number of reagents employed in the sequencing process could effectively be reduced (relative to adding an additional scavenger composition such as BB7), we combined the scavenger with the Scan Mix to generate the ScavScan composition and used the ScavScan composition during both the scan (detection) and PCW steps. The PCW step in these tests were compared to the use of the Scan Mix (VSM) for the scan step and BB7 for the PCW step as a baseline. More particularly, the baseline PCW included a first wash with BB2, a second wash with BB7, and a third wash with BB2 (e.g., BB2/BB7/BB2=Baseline).

When using the "ScavScan" mix in both the scan step and as the PCW step, about 20% more phasing than baseline was observed, despite using the scavenger compound in the scan mix. See FIG. 6 in which phasing rates are shown along the vertical axis. More particularly, the PCW included a first wash with ScavScan and a second wash with BB2 (e.g., ScavScan/BB2).

To neutralize the increase in phasing when using ScavSvan in the PCW wash step, three alternative strategies were evaluated:

Increase the volume from 100 uL to 200 uL of universal buffer ("BB2") wash performed after washing with ScavScan;

Increase the buffer strength of the BB2 buffer universally from 50 mM to 150 mM ("BB2+"); and Reformulate scan mix.

Figure 6:
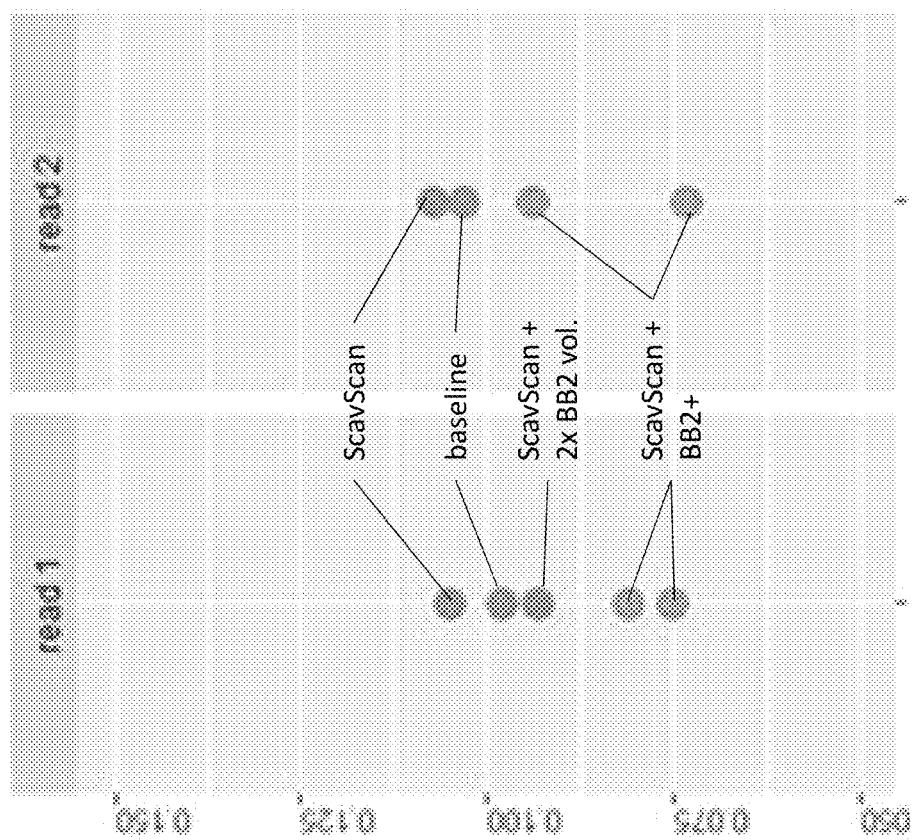
FIG. 6 is a plot of rate of phasing employing different compositions in the scanning step, the post-cleave wash step, or the scanning step and the post-cleave wash step.

As shown in the plot in FIG. 6 doubling the volume of BB2 wash and increasing the BB2 buffer strength (BB2+) reduced phasing relative to baseline. That is, the PCW step included a first wash with ScavScan and a second wash with twice as much BB2 (e.g., ScavScan/2xBB2 vol). Further increasing the volume of the BB2 wash to 250 uL or 500 uL did not result in further improvements (reduction) in phasing (data not shown).

It is noted that doubling the wash volume may result in increased cycle times, and thus may, in some circumstances, be less desirable than increasing the BB2 buffer strength (BB2+). In addition, doubling the BB2 volume may result in the need for larger buffer cartridges or containers which may undesirably increase the footprint or size of the sequencing apparatus employing the cartridge or container and may increase the cost of shipping and manufacturing the cartridges, containers, and compositions.

It is also noted that increasing the buffer strength produced less phasing than doubling the BB2 wash volume. See FIG. 6. Accordingly, increasing the buffer strength of the universal buffer may be more desirable, in certain circumstances, than increasing the wash volume. However, because the universal wash buffer may be used at various stages of sequencing and beyond (e.g. clustering on flow cell, etc.), the effects of increasing the buffer strength of the universal buffer should be considered carefully, particularly if only one universal buffer is to be employed.

Figure 7A:
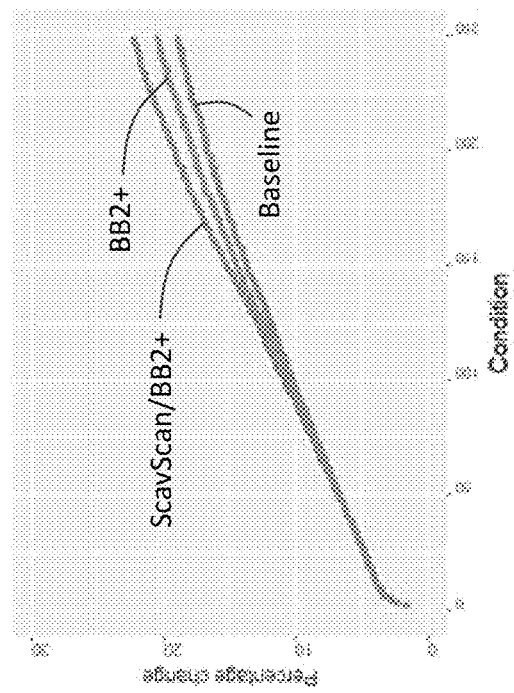
FIG. 7A-C are plots of error rate (A), pre-phasing (B), and phasing (C) employing different compositions in the scanning step, the post-cleave wash step, or the scanning step and the post-cleave wash step.
Figure 7B:
Figure 7C:
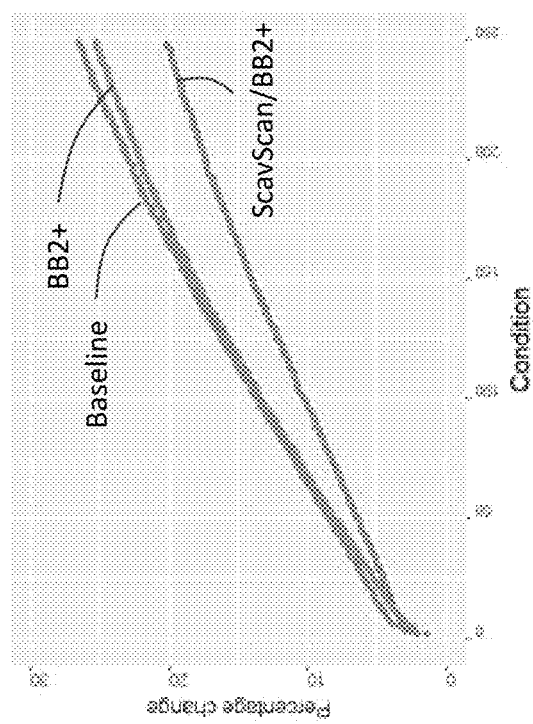

We determined the error rate, rate of pre-phasing, and rate of phasing using baseline conditions (Scan mix, VSM, for scanning and BB7 with BB2 wash for PCW), ScavScan/BB2+ conditions (ScavScan for scanning and ScavScan with BB2+ for PCW), and for BB2+ conditions (Scan Mix, VSM, for scanning and BB7/BB2+ for PCW). 250 cycles of sequencing were performed on an Illumina, Inc. MiniSeq® sequencer (sequencer was modified to allow 250 cycles). The results are presented in FIGS. 7A-C (Error rate in FIG. 7A, pre-phasing in FIG. 7B, and phasing in FIG. 7C). The results indicate that long reads with acceptable error rates are possible when BB2+ replaces BB2 universally, particularly when used with ScavScan.

We determined the effect of increasing the universal buffer concentration without using a scavenger in the PCW. That is, we employed the Scan Mix (VSM) for the scan and the following compositions for the PCW: BB2 alone and with 10 mM lipoic acid (i.e., BB7), BB2+ alone and with 10 mM lipoic acid, BB2++ alone and with 10 mM lipoic acid, and BB2+++ alone and with 10 mM lipoic acid. BB2++ is the same as BB2+, except that BB2++ has 300 mM Tris. BB2+++ is the same as BB2+, except that BB2+++ has 600 mM Tris. Improvements (reductions) in pre-phasing occur with increasing the buffer strength of the universal wash composition without a scavenger. However, the pre-phasing remains higher than the lowest buffer strength universal wash (BB2) with a scavenger. In addition, further improvements were observed with increased buffer strength (BB2+, BB2++, and BB2+++). Unlike wash compositions without the scavenger, wash compositions with the scavenger did not result in additional improvements with further increases in buffer strength (e.g., BB2++ and BB2+++ were not substantially different than BB2+).

We evaluated the ability of scavengers other than lipoic acid to improve sequencing.

Specifically, we replaced lipoic acid in BB7 and ScavScan buffers with 1 mM cystine, 10 mM 3,3'-dithiodipropionic acid (DPPA), and 10 mM pegylated (Cs) azide. Cystine and pegylated azide resulted in increased pre-phasing relative to both BB7 and ScavScan, while DPPA resulted in similar phasing.

Figure 8:
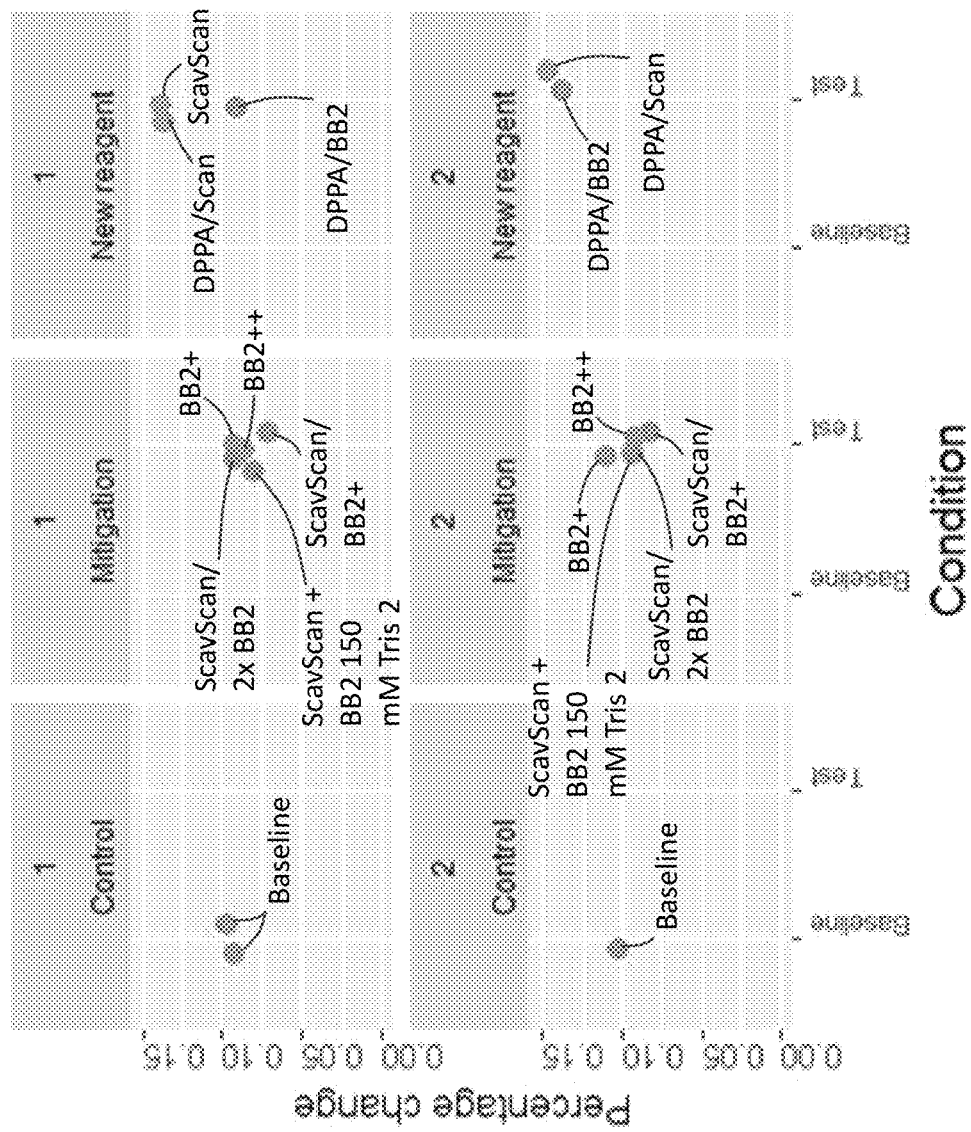
FIG. 8 shows plots of the effect of phasing when different compositions were employed in the scanning step, the post-cleave wash step, or the scanning step and the post-cleave wash step.

Results on phasing when using the various DDPA compositions in the PCW wash are shown in FIG. 8. As shown, DPPA had similar effects on phasing as lipoic acid. As shown in the upper right plot, DPPA performed better in lower Tris buffer strength (50 mM Tris for BB2, 1M Tris for Scan). The post cleavage wash conditions employed to generate the results shown in FIG. 8 were:

Baseline (BB7 with BB2 wash)
ScavScan/2xBB2 (ScavScan with twice the volume (relative to baseline) of BB2 wash)
BB2+ (baseline with universal wash, BB2, modified to have 150 mM Tris)
BB2++ (baseline with universal wash, BB2, modified to have 300 mM Tris)
ScavScan/BB2+ (ScavScan with BB2+ wash)
ScavScan BB2 150 mM Tris 2: Repeat of ScavScan/BB2+
DPPA/Scan (10 mM DPPA added to Scan Mix, VSM)
DPPA/BB2 (10 mM DPPA added to BB2)

We also compared phasing and pre-phasing between PCW washes that included lipoic acid as a scavenger and DPPA as a scavenger. Specifically, 250 cycles on an Illumina, Inc. MiniSeq® sequencer were run using the following compositions for the PCW wash step:

Baseline (BB7 with BB2 wash)
BB2+ (BB7 with universal wash, BB2, modified to have 150 mM Tris)
ScavScan/BB2+ (ScavScan with BB2+ wash)
DPPA (10 mM DPPA added to BB2, BB2 wash)

Figure 9A:
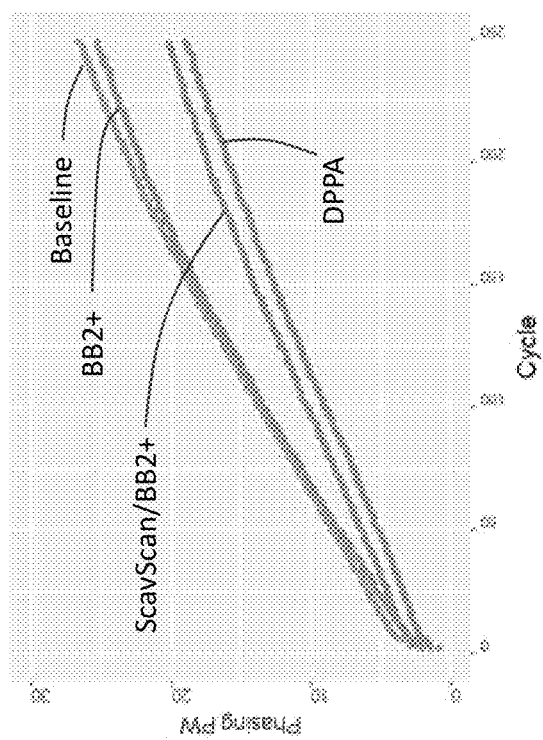
FIGS. 9A-B show plots of phasing (A) and pre-phasing (B) in when different compositions were employed in the scanning step, the post-cleave wash step, or the scanning step and the post-cleave wash steps.
Figure 9B:
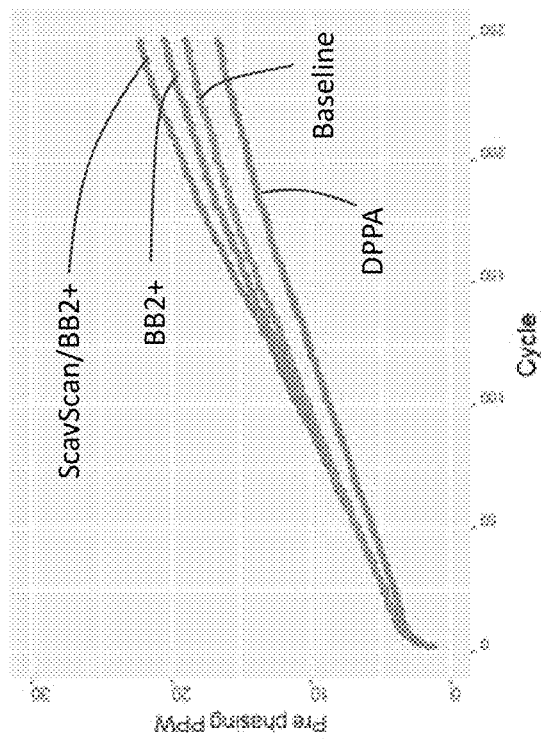

As show in FIGS. 9A and 9B, DPPA resulted in lower phasing and pre-phasing than both baseline and ScavScan/BB2+.

A number of embodiments have been described. Nevertheless, it will be understood that various modifications may be made. Accordingly, other embodiments are within the scope of the following claims.

What is claimed is:

1. A polynucleotide sequencing method comprising:
   (a) incorporating a blocked, labeled nucleotide into a copy polynucleotide strand complementary to at least a portion of a template polynucleotide strand;
   (b) identifying the blocked, labeled nucleotide in the presence of a first buffer composition;
   (c) chemically removing a label and blocking moiety from the blocked, labeled nucleotide incorporated into the copy strand; and
   (d) washing the chemically removed label and blocking moiety away from the copy strand with a wash solution comprising the first buffer composition, wherein the washing results in a reduced error rate or phasing,
   wherein the first buffer composition comprises an antioxidant and a scavenger compound.

2. The method of claim 1, further comprising repeating steps (a) to (d) until a sequence of the portion of the template polynucleotide strand is determined.

3. The method of claim 1, wherein the scavenger compound comprises a disulfide moiety or an azide moiety.

4. The method of claim 3, wherein the scavenger compound comprises a disulfide moiety.

5. The method of claim 3, wherein the scavenger compound is lipoic acid or 3,3'-dithiodipropionic acid (DDPA).

6. The method of claim 1, wherein removing the label and the blocking moiety from the blocked, labeled nucleotide incorporated into a copy polynucleotide strand comprises contacting the copy strand with tris(hydroxymethyl)phosphine.

7. The method of claim 1, wherein the first buffer composition comprises an antioxidant selected from the group consisting of ascorbate, acetovanillone, and 6-hydroxy-2,5,7,8-tetramethylchroman-2-carboxylic acid.

8. The method of claim 1, wherein the template polynucleotide strand is attached to a solid support.

9. The method of claim 8, wherein the template polynucleotide is attached to a flow cell.

10. A polynucleotide sequencing method comprising:
    removing a label and a blocking moiety from a blocked, labeled nucleotide incorporated into a copy polynucleotide strand that is complementary to at least a portion of a template polynucleotide strand; and
    washing the removed label and blocking moiety away from the copy strand with a wash solution comprising 3,3'-dithiodipropionic acid (DDPA), wherein the washing results in a reduced error rate or phasing.

11. The method of claim 10, further comprising:
    identifying the blocked, labeled nucleotide incorporated into the copy strand prior to chemically removing the blocked, labeled nucleotide,
    wherein detecting the identity of the blocked, labeled nucleotide occurs in the presence of a buffer composition comprising DDPA.

* * * * *